US009603601B2

(12) United States Patent
Tegels

(10) Patent No.: US 9,603,601 B2
(45) Date of Patent: Mar. 28, 2017

(54) OCCLUSION DEVICES INCLUDING DUAL BALLOONS AND RELATED METHODS

(71) Applicant: St. Jude Medical Puerto Rico LLC, Caguas, PR (US)

(72) Inventor: Zachary J. Tegels, Minneapolis, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 638 days.

(21) Appl. No.: 13/758,890

(22) Filed: Feb. 4, 2013

(65) Prior Publication Data

US 2014/0222056 A1   Aug. 7, 2014

(51) Int. Cl.
 A61B 17/12 (2006.01)
 A61M 25/10 (2013.01)
 A61B 17/00 (2006.01)

(52) U.S. Cl.
 CPC .... *A61B 17/12136* (2013.01); *A61B 17/0057* (2013.01); *A61M 25/1011* (2013.01); *A61B 17/12109* (2013.01); *A61B 2017/00646* (2013.01); *A61B 2017/12127* (2013.01); *Y10T 29/49826* (2015.01)

(58) Field of Classification Search
 CPC .......... A61B 17/12136; A61B 17/0057; A61B 17/12109; A61M 25/1011; A61M 2025/1013; A61M 2025/1015; A61M 25/0029; A61M 25/001; A61M 25/0014; A61M 2025/0034; A61M 2025/0037; Y10T 29/49826
 See application file for complete search history.

(56) References Cited

U.S. PATENT DOCUMENTS

| 5,188,593 | A | * | 2/1993 | Martin | A61M 5/1582 604/43 |
| 5,368,049 | A | * | 11/1994 | Raman | A61M 25/09 600/434 |
| 5,374,245 | A | * | 12/1994 | Mahurkar | A61M 25/001 604/43 |
| 5,720,735 | A | * | 2/1998 | Dorros | A61F 2/90 604/284 |
| 6,210,380 | B1 | * | 4/2001 | Mauch | A61F 2/954 604/284 |
| 2005/0033237 | A1 | * | 2/2005 | Fentress | A61M 25/0009 604/165.03 |

* cited by examiner

*Primary Examiner* — Sarah W Aleman
(74) *Attorney, Agent, or Firm* — Holland & Hart

(57) ABSTRACT

An occlusion device may comprise a first tube having a first balloon positioned at a distal end, and a second tube having a second balloon positioned at a distal end. The first balloon may be sized and configured to occlude a vascular lumen upstream of a vascular puncture, and the second balloon may be sized and configured to simultaneously occlude the vascular lumen downstream of the vascular puncture. A method of occluding a vascular puncture may comprise positioning a distal end of an occlusion device comprising a first balloon and a second balloon through the vascular puncture and into a vascular lumen. The first balloon may be positioned downstream of the vascular puncture, and the second balloon may be positioning upstream of the vascular puncture.

11 Claims, 5 Drawing Sheets

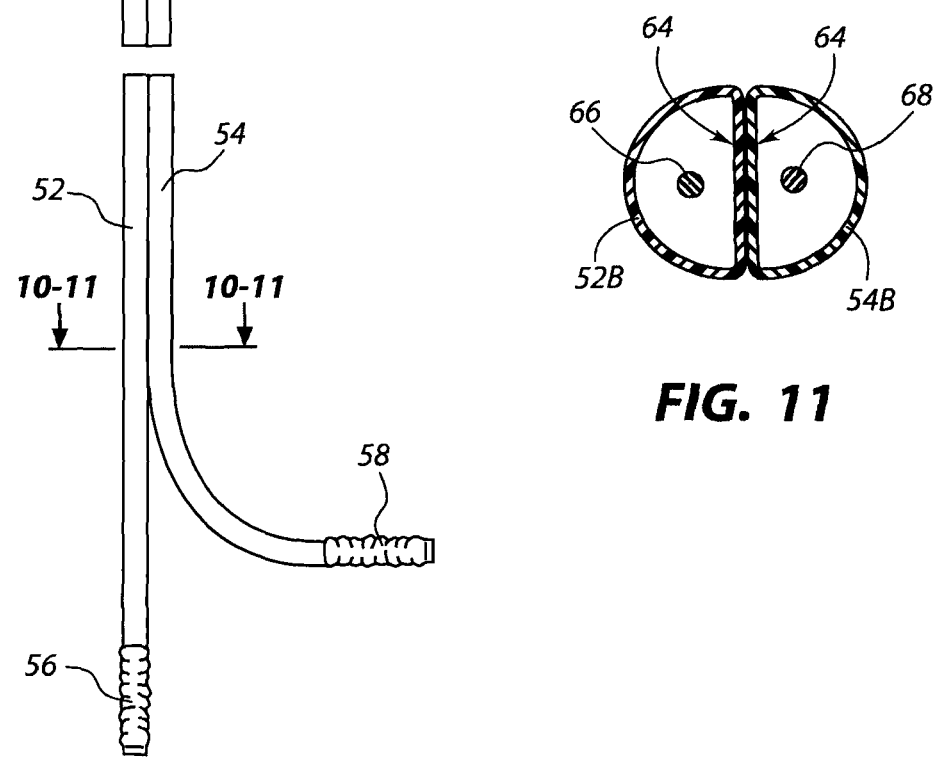
FIG. 9
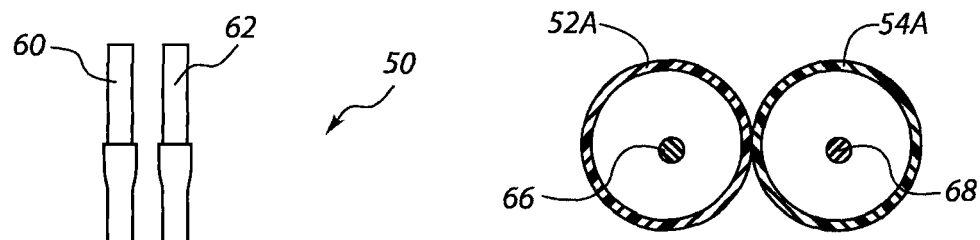
FIG. 10
FIG. 11

OCCLUSION DEVICES INCLUDING DUAL BALLOONS AND RELATED METHODS

TECHNICAL FIELD

The present disclosure relates generally to vascular occlusion devices. More specifically, the present disclosure relates to vascular occlusion devices that include two balloons for vascular occlusion upstream and downstream from a vascular puncture and to related methods.

BACKGROUND

Various surgical procedures are routinely carried out intravascularly or intraluminally. For example, in the treatment of vascular disease, such as arteriosclerosis, it is a common practice to access the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., catheters) may pass through the sheath to an operative position within the artery. Intravascular and intraluminal procedures unavoidably present the problem of stopping the bleeding at the percutaneous puncture after the procedure has been completed and after the instruments (and any insertion sheaths used therewith) have been removed.

Some devices are available to provide temporary hemostasis through the vascular puncture by positioning a balloon near the large bore access location; however, access must be gained via a second vascular puncture on the collateral side. Such devices are not configured to provide temporary hemostasis without utilizing a separate access location. Thus, to achieve temporary hemostasis without utilizing a separate access location, manual pressure must be applied to an outer skin surface of the patient upstream of the percutaneous puncture.

SUMMARY

One aspect of the present disclosure relates to occlusion devices comprising a first tube having a first balloon positioned at a distal end, and a second tube having a second balloon positioned at a distal end, each of the first and second tubes configured to extend through a vascular puncture and into a vascular lumen. The first balloon may be sized and configured to occlude the vascular lumen upstream of the vascular puncture, and the second balloon may be sized and configured to simultaneously occlude the vascular lumen downstream of the vascular puncture.

The first tube and the second tube may each comprise an outer diameter between about 0.030 inch and about 0.036 inch. The device may further comprise a third tube, a distal end of the third tube in fluid communication with and coupled to both a proximal end of the first tube and a proximal end of the second tube. The third tube may comprise an outer diameter between about 0.030 inch and about 0.036 inch. The device may further comprise a fluid source in fluid communication with both the first balloon and the second balloon. Additionally, the first balloon may be in fluid communication with the second balloon.

The first tube may have a circular cross-sectional shape perpendicular to a longitudinal axis of the first tube, and the second tube may have a circular cross-sectional shape perpendicular to a longitudinal axis of the second tube. Alternatively, the first tube may have a D-shaped cross-section perpendicular to a longitudinal axis of the first tube, and the second tube may have a D-shaped cross-section perpendicular to a longitudinal axis of the second tube. Additionally, the device may further comprise a first fluid source in fluid communication with the first balloon and a separate second fluid source in fluid communication with the second balloon.

The device may further comprise a first structural support wire extending through the first tube and first balloon, and a second structural support wire extending through the second tube and the second balloon. At least one of the first structural support wire and the second structural support wire may comprise stainless steel. Additionally, at least one of the first structural support wire and the second structural support wire may comprise at least one of a shape memory alloy and a superelastic alloy. For example, at least one of the first structural support wire and the second structural support wire may comprise a nickel-titanium alloy.

Another aspect of the present disclosure relates to a method of occluding a vascular puncture. The method may comprise positioning a distal end of an occlusion device comprising a first balloon and a second balloon through the vascular puncture and into a vascular lumen. The first balloon may be positioned downstream of the vascular puncture, and the second balloon may be positioning upstream of the vascular puncture. The first balloon may be inflated to occlude the vascular lumen downstream of the vascular puncture, and the second balloon may be inflated to occlude the vascular lumen upstream of the vascular puncture.

The method may further comprise directing at least one of the first balloon and the second balloon with an internal structural support wire. The method may further include directing at least one of the first balloon and the second balloon with an internal structural support wire comprising stainless steel. The method may include directing at least one of the first balloon and the second balloon with an internal structural support wire comprising a nickel-titanium alloy. Additionally, the method may include directing fluid from a fluid source into the first balloon and the second balloon substantially simultaneously.

A further aspect of the present disclosure relates to a method of manufacturing an occlusion device. The method may comprise providing a first tube comprising a first balloon located at a distal end, the first balloon sized and configured to extend through a vascular puncture and occlude a vascular lumen upstream of the vascular puncture. A second tube comprising a second balloon located at a distal end may also be provided, the second balloon sized and configured to extend through a vascular puncture and to occlude the vascular lumen downstream of the vascular puncture. Additionally, a proximal end of the first tube may be coupled to a proximal end of the second tube.

The method may further comprise coupling the proximal end of the first tube and the proximal end of the second tube to a distal end of a third tube.

BRIEF DESCRIPTION OF THE DRAWINGS

The accompanying drawings illustrate various embodiments of the present methods and systems and are a part of the specification. The illustrated embodiments are merely examples of the present systems and methods and do not limit the scope thereof.

FIG. 9 is a side view of an occlusion device according to an embodiment of the present disclosure wherein fluid channels of a first tube and a second tube remain separate.

FIG. 10 is a cross-sectional view of the first tube and a second tube of an occlusion device such as shown in FIG. 9, wherein the first and second tubes have a circular shaped cross-section.

FIG. 11 is a cross-sectional view of the first tube and a second tube of an occlusion device such as shown in FIG. 9, wherein the first and second tubes have a D-shaped cross-section.

DETAILED DESCRIPTION

The devices and systems disclosed herein may be used to close or seal percutaneous punctures made through the body tissue of a patient to gain access to a body cavity of a patient. Access through these percutaneous punctures allows a physician to carry out various procedures in or through the body cavity for examination, surgery, treatment and the like. While not meant to be limiting, the systems are illustrated being used to seal percutaneous punctures that provide access to vascular lumens in patients for various procedures. It will be appreciated that the systems are applicable to other procedures requiring sealing of a puncture through body tissue into a cavity including, for example, laparoscopic surgery and other surgery techniques using a relatively small incision.

While the vascular instruments shown and described below include procedural sheaths and puncture sealing devices, the application of principles described herein are not limited to the specific devices shown. The principles described herein may be used with any medical device. Therefore, while the description below is directed primarily to arterial procedures and certain embodiments of a vascular closure device, the methods and apparatus are only limited by the appended claims. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

As used in this specification and the appended claims, the term "tube" is an elongated device with a passageway. The passageway may be enclosed or open (e.g., a trough). A "lumen", when referring to a bodily organ, refers to any open space or cavity in the bodily organ, especially in a blood vessel. The words "including" and "having," as well as their derivatives, as used in the specification, including the claims, have the same meaning as the word "comprising."

Figure 1:
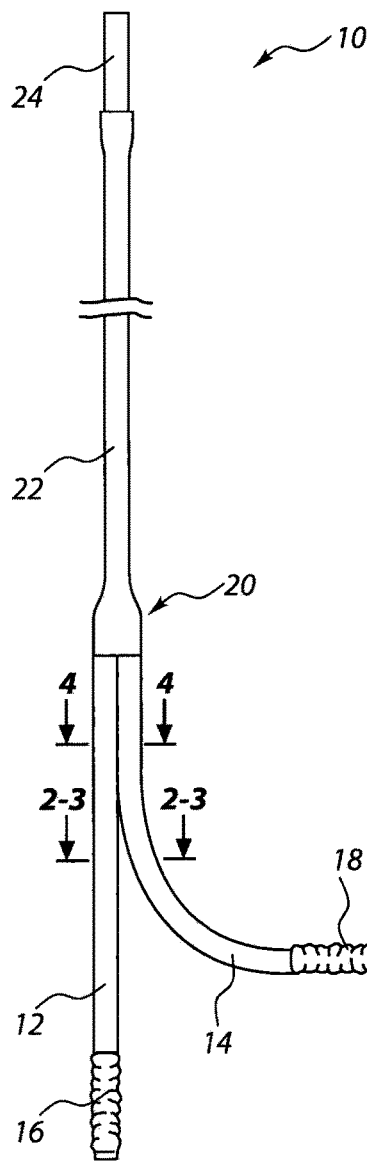
FIG. 1 is a side view of an occlusion device according to an embodiment of the present disclosure.

As shown in FIG. 1, a vascular occlusion device 10 may comprise a first tube 12 and second tube 14. A first balloon 16 may be located at a distal end of the first tube 12, and a second balloon 18 may be located at a distal end of the second tube 14. A proximal end of the first tube 12 may be coupled to a proximal end of the second tube 14 at a joint 20. Additionally, the proximal end of the first tube 12 and the proximal end of the second tube 14 may be coupled to and in fluid communication with a third tube 22 via the joint 20. A proximal end of the third tube 22 may be coupled to a hypotube 24, such as a stainless steel hypotube having a polymer overjacket.

Figure 8:
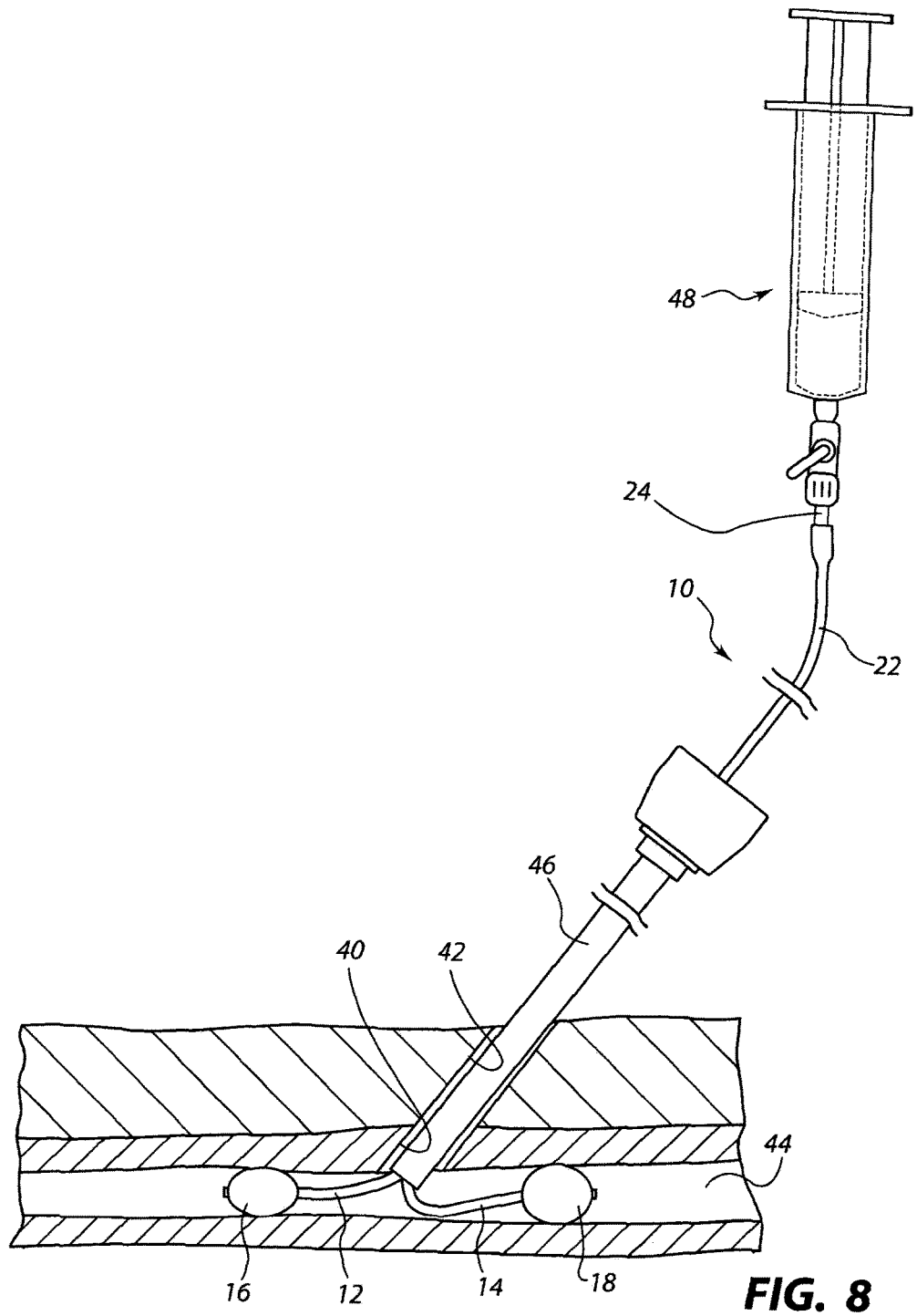
FIG. 8 is a side view of the occlusion device of FIG. 1 inserted through a vascular puncture, wherein the balloons are inflated to occlude blood flow.

The first balloon 16 may be sized and configured to occlude a vascular lumen upstream of a vascular puncture, and the second balloon 18 may be sized and configured to simultaneously occlude the vascular lumen downstream of the vascular puncture (see FIG. 8).

Each of the first and second tubes 12 and 14 may be sized with a relatively small outer diameter. As a non-limiting example, each of the first tube 12 and the second tube 14 may comprise an outer diameter sized between about 0.030 inch and about 0.036 inch. This may facilitate access through a relatively small vascular opening.

The third tube 22 may be sized similarly to the first tube 12 and the second tube 14. As a non-limiting example, the third tube 22 may comprise an outer diameter sized between about 0.030 inch and about 0.036 inch.

Each of the first, second and third tubes 12, 14 and 22 may be made of a polymer material, such as a thermoplastic elastomer. For example, each of the first, second and third tubes 12, 14 and 22 may be made of a polyether block amide made of a flexible polyether and a rigid polyamide, such as the polymer sold under the trade name PEBAX® available from Arkema of Colombes, France.

Figure 2:
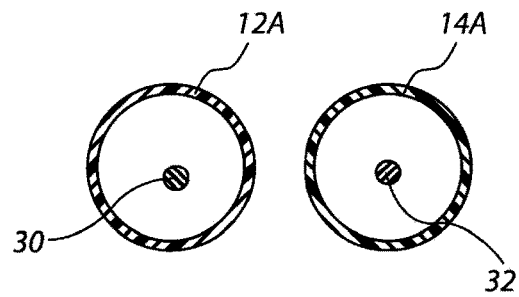
FIG. 2 is a cross-sectional view of a first tube and a second tube of an occlusion device such as shown in FIG. 1, wherein the first and second tubes have a circular shaped cross-section.

As shown in FIG. 2, in some embodiments the first tube 12A may have a circular cross-sectional shape perpendicular to a longitudinal axis of the first tube 12A. The second tube 14A may also have a circular cross-sectional shape perpendicular to a longitudinal axis of the second tube 14A.

Figure 3:
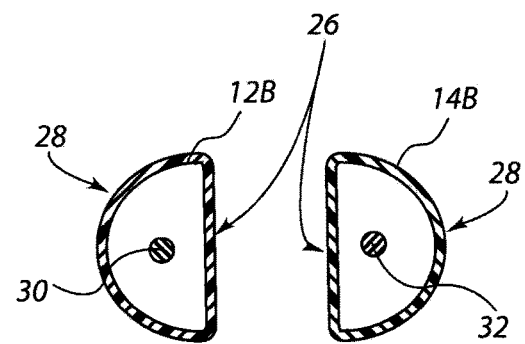
FIG. 3 is a cross-sectional view of a first tube and a second tube of an occlusion device such as shown in FIG. 1, wherein the first and second tubes have a D-shaped cross-section.

In further embodiments, as shown in FIG. 3, the first tube 12B may have a D-shaped cross-section perpendicular to a longitudinal axis of the first tube 12B. Similarly, the second tube 14B may have a D-shaped cross-section perpendicular to a longitudinal axis of the second tube 14B. The D-shaped cross section may be defined by a cross-sectional shape similar in appearance to the uppercase letter D (i.e., shaped generally as a semicircle). A portion of the D-shaped cross-section may be defined by a substantially planar wall 26 (i.e., a flat wall). Another portion of the D-shaped cross-section may be defined by an arcuate wall 28 (i.e., a curved wall) joined to the substantially planar wall 26. In further embodiments, other cross-sectional shapes may be utilized, for example the first and second tubes 12 and 14 may comprise one or more of an oval cross-sectional shape and a polygonal cross-sectional shape.

Figure 4:
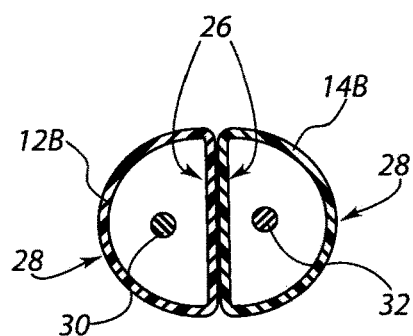
FIG. 4 is a cross-sectional view of the first and second tubes of FIG. 3, wherein the first and second tubes are in mutual contact.

The vascular occlusion device 10 may be assembled with the substantially planar wall 26 of the first tube 12B positioned adjacent to the substantially planar wall 26 of the second tube 14B. Accordingly, the first and second tubes 12B and 14B may be positioned in mutual contact to define a combined cross-section that is generally circular in shape, as shown in FIG. 4. In view of this, the first and second tubes 12B and 14B having a D-shaped cross-section may have a smaller outer profile when positioned in mutual contact when compared to two circular tubes of a similar size in mutual contact. This combined shape may facilitate access through a relatively small vascular opening. Additionally, this combined shape may facilitate a partial closure of a relatively large vascular puncture, such as by installing sutures, while the first and second tubes 12B and 14B are extending through the vascular puncture and the first and second balloons 16 and 18 are positioned to occlude blood flow.

In some embodiments, the vascular occlusion device 10 may be configured such that the distal end, including the first and second tubes 12 and 14 and the first and second balloons 16 and 18 has a maximum cross-sectional diameter between about 0.045 inch and about 0.050 inch (when the first and second balloons 16 and 18 are fully deflated). This relatively small cross-sectional area may facilitate the removal of the distal end of the vascular occlusion device 10 from a percutaneous access site after sutures have been tied. Additionally, it may facilitate the use of the vascular occlusion device 10 as a bailout option to achieve hemostasis in the event that the suture tying fails.

The hypotube 24 coupled to the proximal end of the third tube 22 may facilitate the attachment of a fluid source to the vascular occlusion device 10. A valve, such as a Touhy-Borst valve, may be coupled to the hypotube 24 and provide fluid communication between a fluid source, such as a fluid filled syringe, and the third tube 22 (see FIG. 8). The third tube 22 may provide a fluid path to the first and second tubes 12 and 14. Likewise, the first tube 12 may provide a fluid path to the first balloon 16, and the second tube 14 may provide a fluid path to the second balloon 18. Accordingly, the fluid source may be in fluid communication with both the first balloon 16 and the second balloon 18. Additionally, the first balloon 16 may be in fluid communication with the second balloon 18 and the first and second balloons 16 and 18 may be maintained at substantially the same pressure.

Figures 5, 6:
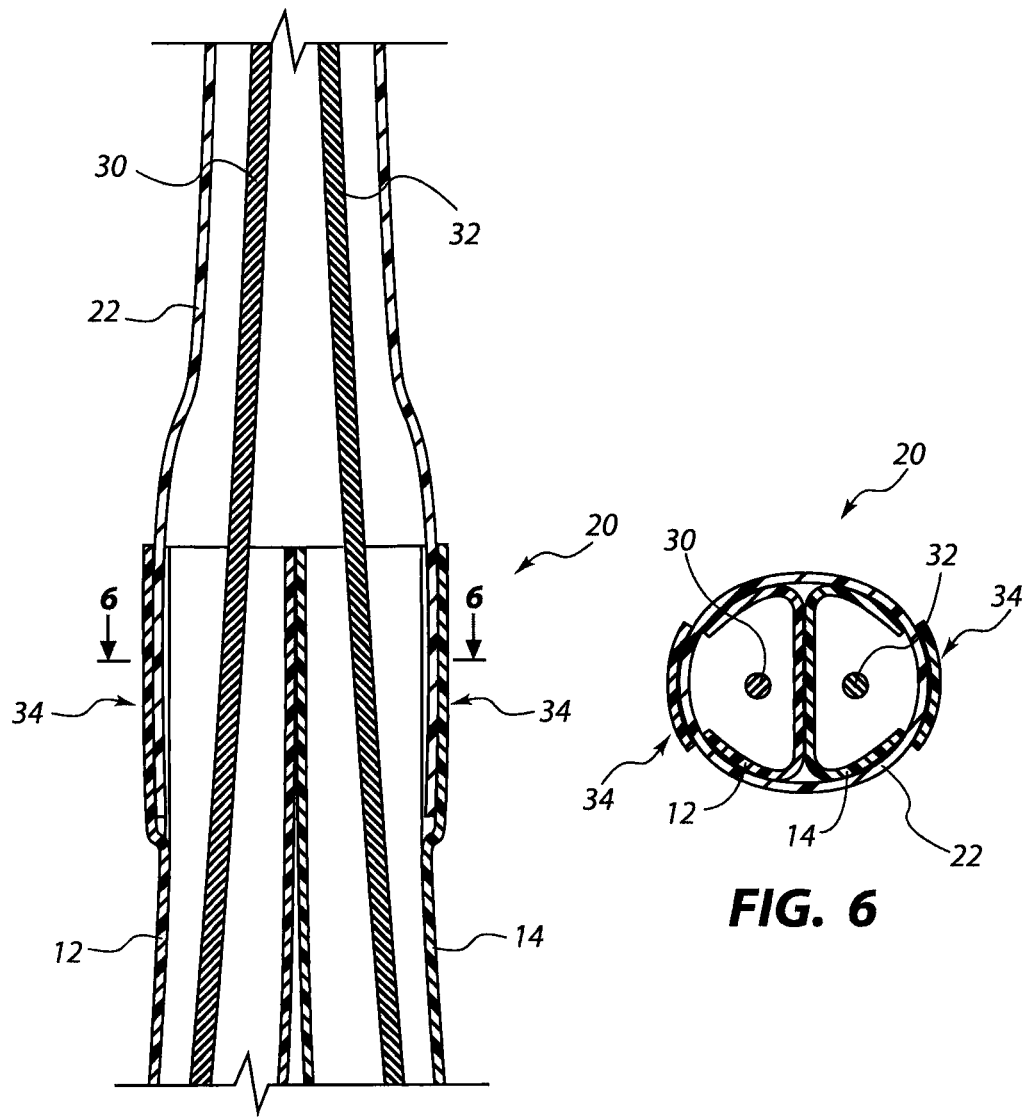
FIG. 5 is a cross-sectional view of a joint of the occlusion device shown in FIG. 1.
FIG. 6 is a perpendicular cross-sectional view of the joint of FIG. 5.

As shown in FIG. 5, a first structural support wire 30 may extend through the first tube 12 and the first balloon 16. Additionally, a second structural support wire 32 may extend through the second tube 14 and the second balloon 18. The structural support wires 30 and 32 may provide support for each of the first and second tubes 12 and 14, respectively, and assist in directing the first and second balloons 16 and 18 into position within a vascular lumen. In some embodiments, at least one of the first structural support wire 30 and the second structural support wire 32 may comprise stainless steel. In some embodiments, at least one of the first structural support wire 30 and the second structural support wire 32 may comprise at least one of a shape memory alloy and a superelastic alloy, such as a nickel-titanium alloy (e.g., nitinol).

In one embodiment, the first structural support wire 30 may be a stainless steel wire that is relatively straight. Accordingly, the first structural support wire 30 may provide support for the first tube 12 and first balloon 16 to direct the first balloon 16 in a generally forward direction relative to the orientation of the vascular occlusion device 10 within a tissue tract. The tissue tract may be positioned at an acute angle relative to the vascular lumen, with the tissue tract oriented toward a portion of a vascular lumen that is downstream from a vascular puncture. For example the tissue tract may be positioned at an angle between about 30 degrees and about 60 degrees relative to a vascular lumen. Accordingly, a straight wire may cause the first tube to progress forward relative to the tissue tract after insertion into the vascular lumen and facilitate the positioning of the first tube 12 and the first balloon 16 downstream from a vascular puncture (see FIG. 7).

The second structural support wire 32 may be a nitinol wire that is configured to curve away from the first structural support wire 30. Accordingly, the second structural support wire 32 may provide support for the second tube 14 and the second balloon 18 to direct the second balloon 18 around a corner after passing through a vascular opening to direct the second balloon 18 in a rearward direction relative to the orientation of the vascular occlusion device 10 within a tissue tract.

To manufacture the vascular occlusion device 10, the first tube 12 comprising the first balloon 16 located at the distal end and the second tube 14 comprising the second balloon 18 located at the distal end may be provided. The proximal ends of the first and second tubes 12 and 14 may then be coupled together and to the distal end of the third tube 22 by the joint 20.

Referring to FIGS. 5 and 6, to form the joint 20, the distal end of the third tube 22 may be flared. Additionally, a tab 34 may be cut at the proximal end of each of the first and second tubes 12 and 14. The proximal ends of the first and second tubes 12 and 14 may then be inserted into the flared end of the third tube 22, with the tabs 34 extending outside of the third tube 22. A polytetraflouroethylene beading or a mandrel (not shown) may be inserted at the joint 20 and the first, second and third tubes 12, 14 and 22 may be bonded together at the joint 20, such as by a heat shrink process, a reflow process, and/or an adhesive.

Referring again to FIG. 1, the hypotube 24 may then be inserted into the proximal end of the third tube 22 and bonded to the third tube 22, such as by a heat shrink process, a reflow process, and/or an adhesive. Also, the first structural support wire 30 may be inserted through the third tube 22 and into the first tube 12 and the first balloon 16. Likewise, the second structural support wire 32 may be inserted through the third tube 22 and into the second tube 14 and the second balloon 18. Optionally, the proximal ends of the first and second structural support wires 30 and 32 may be welded or otherwise joined to the hypotube 24.

Figure 7:
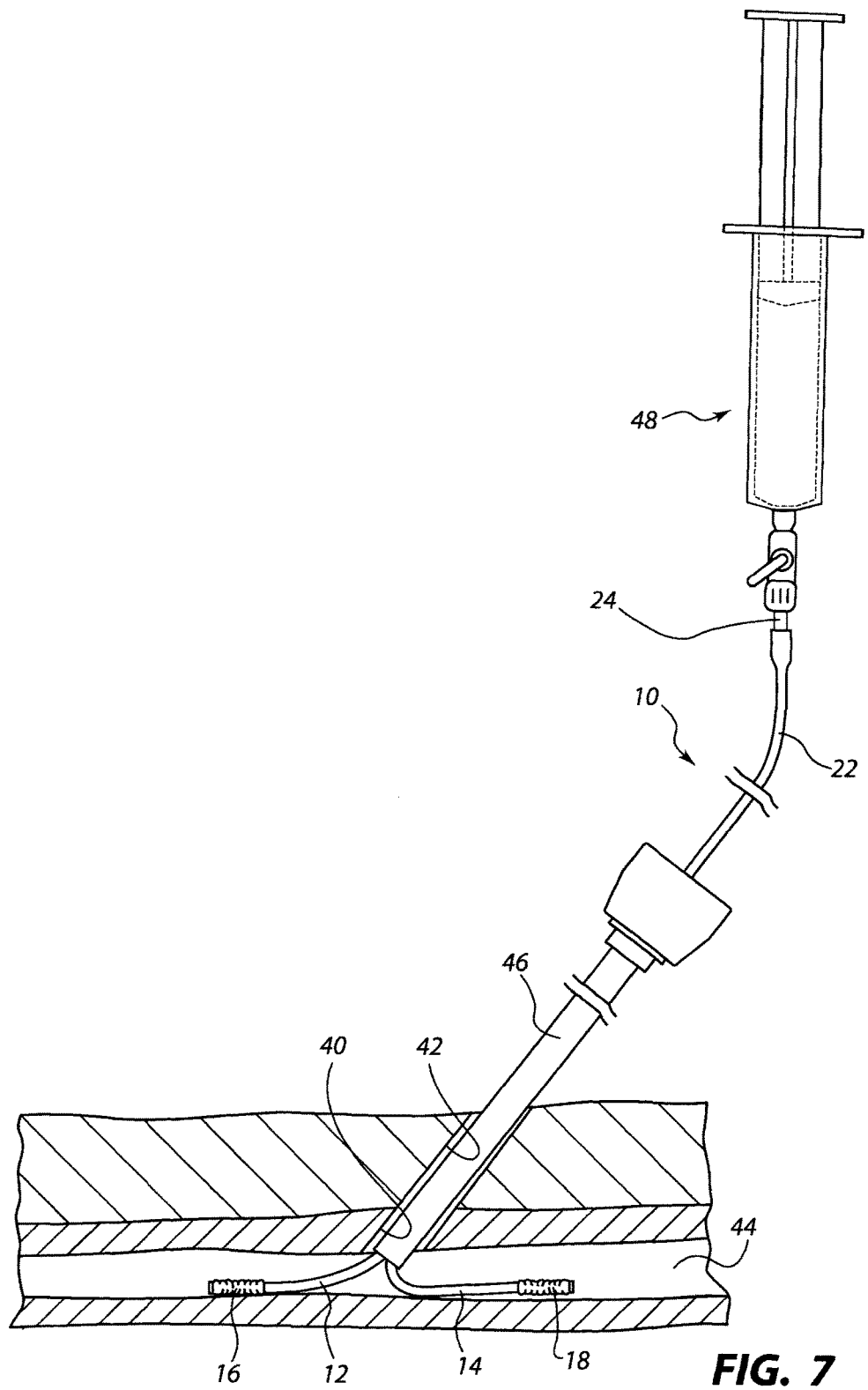
FIG. 7 is a side view of the occlusion device of FIG. 1 inserted through a vascular puncture, wherein balloons of the occlusion device are deflated.

In operation, a vascular lumen 44 may be occluded upstream and downstream of a vascular puncture 40 by the vascular occlusion device 10. Referring to FIG. 7, a distal end of the vascular occlusion device 10, comprising the first balloon 16 and the second balloon 18, may be positioned through a tissue tract 42, through the vascular puncture 40, and into a vascular lumen 44 via a sheath 46. As the first balloon 16 and second balloon 18 are positioned within the vascular lumen 44, the first structural support wire 30 may direct the first balloon 16 forward, which may position the first balloon 16 downstream of the vascular puncture 40. Meanwhile, the second structural support wire 32 may curve rearward and direct the second balloon 18 rearward, which may position the second balloon 18 upstream of the vascular puncture 40.

Referring now to FIG. 8, after the first balloon 16 and the second balloon 18 have been positioned within the vascular lumen 44, fluid may be directed from a fluid source 48 through the third tube 22 to the first and second tubes 12 and 14 to the first and second balloons 16 and 18. For example, a plunger of a syringe coupled to the hypotube 24 may be depressed and a saline solution located within a barrel of the syringe may be directed to the first and second balloons 16 and 18. The fluid may then inflate the first balloon 16 to occlude the vascular lumen 44 downstream of the vascular puncture 40, and substantially simultaneously inflate the second balloon 18 to occlude the vascular lumen 44 upstream of the vascular puncture 40. Accordingly, the first and second balloons 16 and 18 may simultaneously occlude the vascular lumen 44 both upstream and downstream of the vascular puncture 40.

Next, the sheath 46 may be removed from the tissue tract 42 over the vascular occlusion device 10. After the sheath 46 is removed, sutures (not shown) may be inserted through tissue surrounding the vascular puncture 40 and the sutures may be tied to close the vascular puncture 40 around the vascular occlusion device 10. The first and second balloons 16 and 18 of the vascular occlusion device 10 may then be deflated by directing the fluid back to the fluid source 48, and the vascular occlusion device 10 may then be removed from the vascular puncture 40. The sutures may then be tied and the vascular puncture 40 may be closed. In the event that the suture tying fails, the vascular occlusion device 10 may be reinserted and the first and second balloons 16 and 18 may be inflated again to achieve hemostasis through the vascular lumen 44 and consequently stop a source of blood available to access the vascular puncture 40.

In further embodiments, as shown in FIG. 9, a vascular occlusion device 50 may comprise a first tube 52 and second tube 54 having fluid channels that remain separate. A first balloon 56 may be located at a distal end of the first tube 52, and a second balloon 58 may be located at a distal end of the second tube 54. A portion of the first tube 52 and the second tube 54 may be joined together, however, the internal channels within the first and second tubes 52 and 54 may remain separated. A proximal end of the first tube 52 may be coupled to a first hypotube 60, such as a stainless steel hypotube having a polymer overjacket. Similarly, the proximal end of the second tube 54 may be coupled to a second hypotube 62, such as a stainless steel hypotube having a polymer overjacket.

The first balloon 56 may be sized and configured to occlude a vascular lumen upstream of a vascular puncture, and the second balloon 58 may be sized and configured to simultaneously occlude the vascular lumen downstream of the vascular puncture.

Each of the first and second tubes 52 and 54 may be sized with a relatively small outer diameter. As a non-limiting example, each of the first tube 52 and the second tube 54 may comprise an outer diameter sized between about 0.030 inch and about 0.036 inch. This may facilitate access through a relatively small vascular opening.

Each of the first and second tubes 52 and 54 may be made of a polymer material, such as a thermoplastic elastomer. For example, each of the first and second tubes 52 and 54 may be made of a polyether block amide made of a flexible polyether and a rigid polyamide, such as the polymer sold under the trade name PEBAX® available from Arkema of Colombes, France.

In some embodiments, a first tube 52A may have a circular cross-sectional shape perpendicular to a longitudinal axis of the first tube 52A, and a second tube 54A may also have a circular cross-sectional shape perpendicular to a longitudinal axis of the second tube 54A, as shown in FIG. 10. In further embodiments, a first tube 52B may have a D-shaped cross-section perpendicular to a longitudinal axis of the first tube 52B, as shown in FIG. 11. Similarly, a second tube 54B may have a D-shaped cross-section perpendicular to a longitudinal axis of the second tube 54B. In further embodiments, other cross-sectional shapes may be utilized, for example the first and second tubes 52 and 54 may comprise one or more of an oval cross-sectional shape and a polygonal cross-sectional shape.

In embodiments wherein the first and second tubes 52B and 54B have D-shaped cross-sections, as shown in FIG. 11, the vascular occlusion device 50 may be assembled with a substantially planar wall 64 of the first tube 52B positioned adjacent to a substantially planar wall 64 of the second tube 54B. Accordingly, the first and second tubes 52B and 54B may be positioned in mutual contact to define a combined cross-section that is generally circular in shape. In view of this, the first and second tubes 52B and 54B having a D-shaped cross-section may have a smaller outer profile when positioned in mutual contact when compared to two circular tubes of a similar size in mutual contact.

The first hypotube 60 coupled to the proximal end of the first tube 52 may facilitate the attachment of a first fluid source to the vascular occlusion device 10. A valve, such as a Touhy-Borst valve, may be coupled to the first hypotube 60 and provide fluid communication between the first fluid source, such as a fluid filled syringe, and the first tube 52. The first tube 52 may provide a fluid path to the first balloon 56.

Similarly, the second hypotube 62 coupled to the proximal end of the second tube 54 may facilitate the attachment of a second fluid source to the vascular occlusion device 50. A valve, such as a Touhy-Borst valve, may be coupled to the second hypotube 62 and provide fluid communication between the second fluid source, such as a fluid filled syringe, and the second tube 54. The second tube 54 may provide a fluid path to the second balloon 58.

Accordingly, the first and second balloons 56 and 58 may be inflated separately and may be maintained at separate pressures.

A first structural support wire 66 may extend through the first tube 52 and the first balloon 56. Additionally, a second structural support wire 68 may extend through the second tube 54 and the second balloon 58. The first and second structural support wires 66 and 68 may provide support for each of the first and second tubes 52 and 54, respectively, and assist in directing the first and second balloons 56 and 58 into position within a vascular lumen. In some embodiments, at least one of the first structural support wire 66 and the second structural support wire 68 may comprise stainless steel. In some embodiments, at least one of the first structural support wire 66 and the second structural support wire 68 may comprise at least one of a shape memory alloy and a superelastic alloy, such as a nickel-titanium alloy (e.g., nitinol).

In one embodiment, the first structural support wire 66 may be a stainless steel wire that is relatively straight. The second structural support wire 68 may be a nitinol wire that is configured to curve away from the first structural support wire.

To manufacture the vascular occlusion device 50, the first tube 52 comprising the first balloon 56 located at the distal end and the second tube 54 comprising the second balloon 58 located at the distal end may be provided. An exterior portion of the first tube 52 and an exterior portion of the second tube 54 may then be bonded together, such as by a heat shrink process, a reflow process, and/or an adhesive.

The first hypotube 60 may then be inserted into the proximal end of the first tube 52 and bonded to the first tube 52, such as by a heat shrink process, a reflow process, and/or an adhesive. Similarly, the second hypotube 62 may be inserted into the proximal end of the second tube 54 and bonded to the second tube 54, such as by a heat shrink process, a reflow process, and/or an adhesive.

Also, the first structural support wire 66 may be inserted through the first tube 52 and the first balloon 56. Likewise, the second structural support wire 68 may be inserted through the second tube 54 and the second balloon 58. Optionally, the proximal ends of the first and second support wires 66 and 68 may be welded or otherwise joined to the first and second hypotubes 60 and 62, respectively.

In operation, a vascular puncture may be occluded by the vascular occlusion device 50. A distal end of the vascular occlusion device 50, comprising the first balloon 56 and the second balloon 58, may be positioned through a tissue tract, through the vascular puncture, and into a vascular lumen via a sheath. As the first balloon 56 and second balloon 58 are positioned within the vascular lumen, the first structural support wire 66 may direct the first balloon 56 forward, which may position the first balloon 56 downstream of the vascular puncture. Meanwhile, as the second structural support wire 68 may curve rearward and direct the second balloon 58 rearward, which may position the second balloon 58 upstream of the vascular puncture.

After the first balloon 56 and the second balloon 58 have been positioned within the vascular lumen, fluid may be directed from the second fluid source through the second tube 54 to the second balloon 58. For example, a plunger of a syringe coupled to the second hypotube 62 may be depressed and a saline solution located within a barrel of the syringe may be directed to the second balloon 58. The fluid may then inflate the second balloon 58 to occlude the vascular lumen upstream of the vascular puncture.

Similarly, fluid may be directed from the first fluid source through the first tube 52 to the first balloon 56, and the fluid may inflate the first balloon 56 to occlude the vascular lumen downstream of the vascular puncture. Accordingly, the first and second balloons 56 and 58 may simultaneously occlude the vascular lumen both upstream and downstream of the vascular puncture.

Next, the sheath may be removed from the tissue tract over the vascular occlusion device 50. After the sheath is removed, sutures may be inserted in the tissue surrounding the vascular puncture and the sutures may be tied to close the vascular puncture around the vascular occlusion device 50. The first and second balloons 56 and 58 of the vascular occlusion device 50 may then be deflated by directing the fluid back to the first and second fluid sources, respectively, and the vascular occlusion device 50 may then be removed from the vascular puncture. The sutures may then be tied and the vascular puncture may be closed. In the event that the suture tying fails, the vascular occlusion device 50 may be reinserted and the first and second balloons 56 and 58 may be inflated again to achieve hemostasis.

The preceding description has been presented only to illustrate and describe example embodiments of the invention. It is not intended to be exhaustive or to limit the invention to any precise form disclosed. Many modifications and variations are possible in light of the above teachings. It is intended that the scope of the invention be defined by the following claims.

What is claimed is:

1. An occlusion device, comprising:
a first tube comprising a first balloon positioned at a distal end and configured to extend through a vascular puncture into a vascular lumen, the first balloon sized and configured to occlude the vascular lumen upstream of the vascular puncture, the first tube comprising a first tab, the first tab being cut at a proximal end of the first tube;
a second tube comprising a second balloon positioned at a distal end and configured to extend through the vascular puncture and into the vascular lumen, the second balloon sized and configured to simultaneously occlude the vascular lumen downstream of the vascular puncture, the second tube comprising a second tab, the second tab being cut at a proximal end of the second tube;
a first lumen positioned in the first tube;
a first structural support wire extending through the first lumen of the first tube and the first balloon;
a second lumen positioned in the second tube; and
a second structural support wire extending through the second lumen of the second tube and the second balloon;
a third tube, a distal end of the third tube being coupled to the proximal end of the first tube, the distal end of the third tube being coupled to the proximal end of the second tube, the first tab being positioned radially external to an external surface of the third tube, the second tab being positioned radially external to an external surface of the third tube.

2. The occlusion device of claim 1, wherein each of the first tube and the second tube comprise an outer diameter between about 0.030 inch and about 0.036 inch.

3. The occlusion device of claim 1, further comprising a fluid source in fluid communication with both the first balloon and the second balloon.

4. The occlusion device of claim 3, wherein the first balloon is in fluid communication with the second balloon.

5. The occlusion device of claim 1, wherein the first tube has a circular cross-sectional shape perpendicular to a longitudinal axis of the first tube, and the second tube has a circular cross-sectional shape perpendicular to a longitudinal axis of the second tube.

6. The occlusion device of claim 1, wherein the first tube has a D-shaped cross-section perpendicular to a longitudinal axis of the first tube, and the second tube has a D-shaped cross-section perpendicular to a longitudinal axis of the second tube.

7. The occlusion device of claim 1, wherein at least one of the first structural support wire and the second structural support wire is comprised of stainless steel.

8. The occlusion device of claim 1, wherein at least one of the first structural support wire and the second structural support wire comprises at least one of a shape memory alloy and a superelastic alloy.

9. The occlusion device of claim 1, wherein at least one of the first structural support wire and the second structural support wire comprises a nickel-titanium alloy.

10. An occlusion device, comprising:
a first tube comprising a first balloon positioned at a distal end and configured to extend through a vascular puncture into a vascular lumen, the first balloon sized and configured to occlude the vascular lumen upstream of the vascular puncture, the first tube comprising a proximal end, the proximal end of the first tube comprising a first tab;
a second tube comprising a second balloon positioned at a distal end and configured to extend through the vascular puncture and into the vascular lumen, the second balloon sized and configured to simultaneously occlude the vascular lumen downstream of the vascular puncture, the second tube comprising a proximal end, the proximal end of the second tube comprising a second tab;
a first lumen positioned in the first tube;
a first structural support wire extending through the first lumen of the first tube and the first balloon;
a second lumen positioned in the second tube;

a second structural support wire extending through the second lumen of the second tube and the second balloon;

a third tube, a distal end of the third tube being flared, the distal end being in fluid communication with and coupled to the proximal ends of the first and second tubes, the proximal ends of the first and second tubes being positioned within the flared distal end of the third tube with the first and second tabs being positioned radially external to an external surface of the third tube; and a third lumen positioned in the third tube, wherein the first and second structural support wires are positioned in the third lumen.

11. An occlusion device, comprising:

a first tube comprising a first balloon positioned at a distal end and configured to extend through a vascular puncture into a vascular lumen, the first balloon sized and configured to occlude the vascular lumen upstream of the vascular puncture, the first tube comprising a proximal end having a tab portion;

a second tube comprising a second balloon positioned at a distal end and configured to extend through the vascular puncture and into the vascular lumen, the second balloon sized and configured to occlude the vascular lumen downstream of the vascular puncture, the second tube comprising a proximal end having a tab portion;

a first lumen positioned within the first tube;

a first structural support wire extending through the first lumen of the first tube and the first balloon;

a second lumen positioned within the second tube;

a second structural support wire extending through the second lumen of the second tube and the second balloon;

a third tube, a distal end of the third tube being in fluid communication with and coupled to the proximal end of the first tube and the proximal end of the second tube, the tab portions of the first and second tubes being positioned radially external to an external surface of the third tube; and a third lumen positioned within the third tube, wherein the first and second structural support wires extend into the third lumen.

* * * * *